United States Patent
Leonarduzzi et al.

(10) Patent No.: US 11,717,812 B2
(45) Date of Patent: Aug. 8, 2023

(54) CATALYST

(71) Applicant: Velocys Technologies Ltd, Oxford (GB)

(72) Inventors: Daniele Leonarduzzi, Berkshire (GB); Diarmid Roberts, Sheffield (GB); Jay Pritchard, Oxfordshire (GB); Heinz J. Robota, Dublin, OH (US)

(73) Assignee: Velocys Technologies Ltd, Oxford (GB)

(*) Notice: Subject to any disclaimer, the term of this patent is extended or adjusted under 35 U.S.C. 154(b) by 0 days.

(21) Appl. No.: 17/499,369

(22) Filed: Oct. 12, 2021

(65) Prior Publication Data

US 2022/0111363 A1 Apr. 14, 2022

Related U.S. Application Data

(60) Provisional application No. 63/091,097, filed on Oct. 13, 2020, provisional application No. 63/211,804, filed on Jun. 17, 2021.

(30) Foreign Application Priority Data

Nov. 10, 2020 (GB) .................................. 2017710
Jul. 2, 2021 (GB) .................................. 2109611

(51) Int. Cl.
| | |
|---|---|
| *B01J 23/89* | (2006.01) |
| *B01J 21/08* | (2006.01) |
| *B01J 37/02* | (2006.01) |
| *B01J 37/08* | (2006.01) |
| *B01J 35/00* | (2006.01) |
| *B01J 19/00* | (2006.01) |

(Continued)

(52) U.S. Cl.
CPC ....... *B01J 23/8913* (2013.01); *B01J 19/0093* (2013.01); *B01J 21/08* (2013.01); *B01J 23/8986* (2013.01); *B01J 35/0026* (2013.01); *B01J 35/023* (2013.01); *B01J 37/0244* (2013.01); *B01J 37/082* (2013.01); *C07C 1/0435* (2013.01); *C07C 2521/08* (2013.01); *C07C 2523/89* (2013.01)

(58) Field of Classification Search
CPC .... B01J 23/8913; B01J 19/0093; B01J 21/08; B01J 35/0026; B01J 25/023
See application file for complete search history.

(56) References Cited

U.S. PATENT DOCUMENTS

| | | | |
|---|---|---|---|
| 3,540,867 | A | 11/1970 | Baron et al. |
| 4,073,862 | A | 2/1978 | Haese |

(Continued)

FOREIGN PATENT DOCUMENTS

| | | |
|---|---|---|
| CN | 101269848 A | 9/2008 |
| CN | 105505480 A | 4/2016 |

(Continued)

OTHER PUBLICATIONS

Combined Search and Examination Report for related Great Britain Application No. GB2006826.8 dated Aug. 20, 2020.

(Continued)

*Primary Examiner* — Jafar F Parsa
(74) *Attorney, Agent, or Firm* — Renner, Otto, Boisselle & Sklar, LLP

(57) ABSTRACT

The present invention provides a Fischer-Tropsch catalyst comprising greater than about 40% by weight of cobalt, and having a packed apparent bulk density greater than about 1.30 g/mL.

13 Claims, 3 Drawing Sheets

(51) Int. Cl.
    *C07C 1/04*    (2006.01)
    *B01J 35/02*   (2006.01)

(56) References Cited

U.S. PATENT DOCUMENTS

| | | |
|---|---|---|
| 4,810,417 A | 3/1989 | Diemer et al. |
| 5,470,361 A | 11/1995 | Linke et al. |

FOREIGN PATENT DOCUMENTS

| | | |
|---|---|---|
| EP | 0629685 B1 | 1/1991 |
| FR | 2992236 | 12/2013 |
| JP | 201513940 A | 1/2015 |
| RU | 2610526 C2 | 2/2017 |
| WO | 2016011299 | 1/2016 |
| WO | 2016011299 A1 | 1/2016 |

OTHER PUBLICATIONS

Combined Search and Examination Report for related Great Britain Application No. GB2104958.0 dated May 28, 2021.
Cao et al.; "Intensified Fischer-Tropsch synthesis process with microchannel catalytic reactors" Catalysis Today 140 (2009), pp. 149-156.
Rahmati et al., "Chemical and Thermal Sintering of Supported Metals with Emphasis on Cobalt Catalysts During Fischer-Tropsch Synthesis", Chem. Rev. 2020, 120, 4455-4533.
International Search Report for related International Application No. PCT/EP2021/077171 dated Jan. 18, 2022.

CATALYST

This application claims the benefit of U.S. Provisional Patent Application No. 63/091,097, filed Oct. 13, 2020, and U.S. Provisional Patent Application No. 63/211,804, filed Jun. 17, 2021; and claims priority to UK Patent Application No. GB 2017710.1, filed Nov. 10, 2020, and UK Patent Application No. GB 2109611.0, filed Jul. 2, 2021, the disclosures of which are incorporated herein by reference in their entireties.

TECHNICAL FIELD

The present invention concerns a cobalt-containing Fischer-Tropsch catalyst, particularly for use in a microchannel reactor.

BACKGROUND

The Fischer-Tropsch reaction is widely used to generate fuels from carbon monoxide and hydrogen and can be represented by the equation:

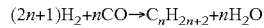

$$(2n+1)H_2 + nCO \rightarrow C_nH_{2n+2} + nH_2O$$

This reaction is highly exothermic and is catalyzed by a Fischer-Tropsch catalyst, typically a cobalt-based catalyst, under conditions of elevated temperature (typically at least 180° C., e.g. 200° C. or above) and pressure (e.g. at least 1000 kPa).

A product mixture is obtained, and n typically encompasses a range from 1 to about 90. It is desirable to minimize light gas (e.g. methane) selectivity, i.e. the proportion of methane (n=1) in the product mixture, and to maximize the selectivity towards C5 and higher (n≥5) paraffins, typically to a level of about 80% or higher, or about 85% or higher. Preferably, at least about 40% w/w of the product mixture has n≥20. This is because shifting selectivity away from lighter products to heavier products increases economic value. There are several factors which affect this selectivity, including operating temperature; a decrease in operating temperature yields a decrease in light hydrocarbon selectivity. The parameter used to compare the selectivity is the Anderson-Schulz-Flory alpha value. The higher the value of alpha, the lower the light hydrocarbon selectivity. At large values of alpha, small changes in alpha can have a significant economic impact on product yields. This is illustrated in Table 1. By way of an example and using the model of Vervloet et al. (*Catal. Sci. Technol.*, 2012, 2, 1221-1233) as a guide, a shift in operating temperature from 210° C. to 200° C. can produce an increase in alpha of 0.03. It is therefore desirable to perform the reaction at a lower temperature, preferably without sacrificing productivity.

TABLE 1

| | Mass fraction of distribution | | |
|---|---|---|---|
| Alpha | C23+ | C40+ | C90+ |
| 0.915 | 0.407 | 0.135 | 0.003 |
| 0.92 | 0.441 | 0.159 | 0.005 |
| 0.93 | 0.515 | 0.220 | 0.011 |
| 0.94 | 0.595 | 0.299 | 0.026 |

The hydrogen and carbon monoxide feedstock is normally synthesis gas.

Unless the context dictates otherwise, any phrase containing the term "synthesis gas" is to be construed to mean a gas primarily comprising hydrogen and carbon monoxide. Other components such as carbon dioxide, nitrogen, argon, water, methane, tars, acid gases, higher molecular weight hydrocarbons, oils, volatile metals, char, phosphorus, halides and ash may optionally also be present.

The use of such terms to describe synthesis gas should not be taken as limiting. The skilled person would understand that each of the terms is construed to mean a gas primarily comprising hydrogen and carbon monoxide.

The synthesis gas may optionally be produced by gasifying a carbonaceous material at an elevated temperature of, for example, at least about 600° C. or higher, or at least about 700° C. or higher, or at least about 800° C. or higher. The carbonaceous material may optionally comprise any carbon-containing material that can be gasified to produce synthesis gas. The carbonaceous material may optionally comprise biomass (e.g., plant or animal matter, biodegradable waste, and the like), a food resource (e.g., as corn, soybean, and the like), and/or a non-food resource such as coal (e.g., low grade coal, high grade coal, clean coal, and the like), oil (e.g., crude oil, heavy oil, tar sand oil, shale oil, and the like), solid waste (e.g., municipal solid waste, hazardous waste), refuse derived fuel (RDF), tires, petroleum coke, trash, garbage, biogas, sewage sludge, animal waste, agricultural waste (e.g., coin stover, switch grass, grass clippings), construction demolition materials, plastic materials (e.g., plastic waste), cotton gin waste, a mixture of two or more thereof, and the like.

Alternatively, synthesis gas may optionally be produced by other means such as by reformation of natural or landfill gas, or of gases produced by anaerobic digestion processes. Also, synthesis gas may optionally be produced by $CO_2$ reforming using electrolysis as a hydrogen source (e.g. so called "electricity-to-fuels" processes).

The synthesis gas, produced as described above, may optionally be treated to adjust the molar ratio of $H_2$ to CO by steam reforming (e.g., a steam methane reforming (SMR) reaction where methane is reacted with steam in the presence of a SMR catalyst); partial oxidation; autothermal reforming; carbon dioxide reforming; water gas shift reaction; or a combination of two or more thereof in preparation for feeding the Fischer-Tropsch catalyst (referred to as fresh synthesis gas).

The term "water gas shift reaction" or "WGS" is to be construed as a thermochemical process comprising converting carbon monoxide and water into hydrogen and carbon dioxide. The synthesis gas obtained after the WGS reaction may be construed to be shifted (i.e. adjusted) synthesis gas.

The molar ratio of $H_2$ to CO in the fresh synthesis gas is preferably in the range from about 1.6:1 to about 2.2:1, or from about 1.8:1 to about 2.1:1, or from about 1.95:1 to about 2.05:1.

The fresh synthesis gas may optionally be combined with a recycled tail gas (e.g. a recycled Fischer-Tropsch tail gas), which also contains $H_2$ and CO, to form a reactant mixture. The tail gas may optionally comprise $H_2$ and CO with a molar ratio of $H_2$ to CO in the range from about 0.5:1 to about 2:1, or from about 0.6:1 to about 1.8:1, or from about 0.7:1 to about 1.2:1.

The aforementioned reactant mixture may optionally comprise $H_2$ and CO in a molar ratio in the range from about 1.4:1 to about 2.1:1, or from about 1.7:1 to about 2.0:1, or from about 1.7:1 to about 1.9:1.

When the recycled tail gas is used, the volumetric ratio of fresh synthesis gas to recycled tail gas used to form the reactant mixture may optionally be in the range from about 1:1 to about 20:1, or from about 1:1 to about 10:1, or from about 1:1 to about 6:1, or from about 1:1 to about 4:1, or from about 3:2 to about 7:3, or about 2:1.

A consequence of the highly exothermic Fischer-Tropsch reaction is the need to remove reaction heat for a commercial-scale process to operate usefully. One approach to this problem is to limit the volumetric productivity such that the rate at which heat is removed can keep appropriate pace with the rate at which heat is produced. This is the principle behind the slurry bubble column reactor and conventional fixed-bed reactor, which are commonly used in the art. Alternatively, by using a reactor design in which the reaction heat can be more effectively removed, such as in a microchannel reactor, it is possible to increase the volumetric productivity many-fold while still maintaining the local reaction temperature within a few degrees of a process target value. This allows for smaller reactors with production rates sufficiently high to achieve economic targets.

One aspect of high volumetric productivity is the higher temporal contaminant burden that a given catalyst volume experiences relative to lower productivity reactors. By way of an example, if the volumetric productivity is 10-fold higher than a typical fixed bed reactor, then the rate of contaminant-related deactivation also becomes roughly 10-fold as high. This requires extremely tight tolerances on the allowable levels of ultra-trace catalyst poisons in the synthesis gas feed.

One potential method of mitigating this problem is to increase the number of reactive sites per unit volume of catalyst charge. Thus, at the same volumetric productivity and at the same time-averaged contaminant concentration, a longer time is required before a charge is rendered uneconomical to operate through poisoning. Such an approach has limited value in either of the two typical reactor systems employed in Fischer-Tropsch synthesis; the slurry bubble column or the conventional fixed bed. In the slurry bubble column, the volumetric productivity is constrained by the allowable solids fraction in the slurry. Consequently, slurry bubble column reactors are inherently constrained with regard to their volumetric productivity well below the productivity typically employed in a Fischer-Tropsch microchannel reactor. In conventional fixed-bed reactors, employing highly engineered catalyst shapes to avoid extensive mass transfer effects on conversion selectivity towards shorter, less economically valuable hydrocarbons, temperature control and process stability will become even more problematic with higher reactive site density. Thus, the present invention is particularly advantageous in microchannel reactors.

In view of the above, it is desirable to increase the number of reactive sites per unit volume of catalyst charge. There are two ways in which this could be achieved:
a) By decreasing the cobalt crystallite size—this will result in an increase in metallic surface area, and consequently an increase in activity. However, this can compromise low methane selectivity and increase deactivation of the catalyst.
b) By increasing the cobalt loading percent—this may increase cobalt metallic surface area and density, but results in a longer catalyst manufacturing procedure.

Catalysts of the art have improved upon either a) or b).

FR2992236 describes a SiC-based catalyst support at least partially covered with $TiO_2$. From 5% to 40% by mass of cobalt is subsequently deposited on said support and used in a Fischer-Tropsch reaction. Table 2 describes three catalysts having 10% by mass of cobalt, and from the data in said table it can be estimated that these catalysts have a packed apparent bulk density (PABD) of cobalt of 0.078-0.084 g/mL.

Cao et al. (*Catalysis Today*, 2009, 140, 149-156) describes the use in a microchannel reactor of an alumina-based cobalt-containing catalyst having a diameter of 150 and 45 μm. However, the catalysts had a cobalt loading of only 30 wt. %.

WO2016011299, which is incorporated herein by reference, describes a composition, comprising $Co_3O_4$, wherein the $Co_3O_4$ in the composition has an average particle size of at least 8.8 nm; and a secondary oxide; and wherein the composition has a porosity of at least 0.35. The composition may optionally comprise from 30 to 60% by weight of cobalt. However, the packed apparent bulk density of cobalt remains relatively low, in the approximate range of 0.4 to 0.49 g/mL.

Therefore, there is a need in the art for catalysts which simultaneously improve upon both a) and b), and thus increase both the cobalt loading and the packed apparent bulk density of the catalyst. It is desirable for the catalysts to have a higher activity and improved contaminant stability whilst maintaining product selectivity, and preferably with a facile synthesis.

SUMMARY OF INVENTION

According to a first aspect of the present invention, there is provided a Fischer-Tropsch catalyst comprising greater than about 40% by weight of cobalt, and having a packed apparent bulk density greater than about 1.30 g/mL.

The catalyst may optionally have a packed apparent bulk density of cobalt greater than about 0.60 g/mL. Therefore, according to another aspect of the present invention, there is provided a Fischer-Tropsch catalyst comprising greater than about 40% by weight of cobalt, and having a packed apparent bulk density of cobalt greater than about 0.60 g/mL.

The inventors have been able to increase both the weight % of cobalt in the catalyst and the packed apparent bulk density of the catalyst, thus resulting in a greater packed apparent bulk density of cobalt. Catalysts of the invention can achieve approximately double the packed apparent bulk density of cobalt compared to catalysts of the art (such as those disclosed in WO2016011299). The inventors have found that this increase in packed apparent bulk density of cobalt leads to increased poison stability, in particular to sulfur and nitrogen poisoning, and greater stability during the lifetime of the catalyst.

The catalyst may optionally comprise greater than about 45% by weight, or greater than about 50% by weight, of cobalt.

The catalyst may optionally comprise no more than about 60% by weight, or no more than about 55% by weight, of cobalt.

The catalyst may optionally comprise from about 40% to about 60% by weight of cobalt, or from about 45% to about 60% by weight of cobalt, or from about 50% to about 60% by weight of cobalt. The catalyst may optionally comprise from about 40% to about 55% by weight of cobalt, or from about 45% to about 55% by weight of cobalt, or from about 50% to about 55% by weight of cobalt.

The catalyst may optionally have a packed apparent bulk density greater than about 1.35 g/mL, or greater than about 1.40 g/mL, or greater than about 1.45 g/mL, or greater than about 1.50 g/mL, or greater than about 1.55 g/mL, or greater than about 1.60 g/mL.

The catalyst may optionally have a packed apparent bulk density of no more than about 1.70 g/mL, or no more than about 1.65 g/mL.

The catalyst may optionally have a packed apparent bulk density from about 1.30 g/mL to about 1.70 g/mL, or from about 1.35 g/mL to about 1.70 g/mL, or from about 1.40 g/mL to about 1.70 g/mL, or from about 1.45 g/mL to about 1.70 g/mL, or from about 1.50 g/mL to about 1.70 g/mL, or from about 1.50 g/mL to about 1.65 g/mL.

The catalyst may optionally have a packed apparent bulk density of cobalt greater than about 0.65 g/mL, or greater than about 0.70 g/mL, or greater than about 0.75 g/mL, or greater than about 0.80 g/mL.

The catalyst may optionally have a packed apparent bulk density of cobalt of no more than about 0.90 g/mL.

The catalyst may optionally have a packed apparent bulk density of cobalt from about 0.60 g/mL to about 0.90 g/mL, or from about 0.65 g/mL to about 0.90 g/mL, or from about 0.70 g/mL to about 0.90 g/mL, or from about 0.75 g/mL to about 0.90 g/mL, or from about 0.80 g/mL to about 0.90 g/mL.

The catalyst may optionally have a cobalt particle size, and/or an average cobalt particle size, of from about 5 nm to about 20 nm, or from about 5 nm to about 15 nm, or from about 6 nm to about 12 nm, or from about 8 nm to about 10 nm. The catalyst may optionally have a cobalt particle size, and/or an average cobalt particle size, of less than about 20 nm, or less than about 19 nm, or less than about 18 nm, or less than about 17 nm, or less than about 16 nm, or less than about 15 nm, or less than about 14 nm, or less than about 13 nm, or less than about 12 nm, or less than about 11 nm. The inventors have found that it is possible to maximize the utilization and efficiency of a high cobalt loading catalyst by ensuring that the cobalt particles are of the appropriate size. It was previously believed that increasing the cobalt loading resulted in an increase in the cobalt particle size (as shown in den Breejen et al., *J. Am. Chem. Soc.* 2009, 131, 20, 7197-7203), and thus a decrease in catalyst efficiency.

The catalyst may optionally comprise at least one noble metal. The noble metal may optionally for example be one or more of Pd, Pt, Rh, Ru, Re, Ir, Au, Ag and Os. Preferably, the noble metal is one or more of ruthenium, rhenium and/or platinum. More preferably, the noble metal is one or more of rhenium and/or platinum. The catalyst may optionally comprise less than about 3% by weight, or less than about 1% by weight, or less than about 0.5% by weight, of noble metals (based on the total weight of the catalyst). The catalyst may optionally comprise from about 0.01% to about 3% by weight, or from about 0.05% to about 1% by weight, or from about 0.1% to about 0.5% by weight, of noble metals (based on the total weight of the catalyst).

The catalyst may optionally comprise one or more other metal-based components as promoters or modifiers. These metal-based components may optionally also be present in the catalyst as carbides, oxides or elemental metals. A suitable metal for the one or more other metal-based components may optionally for example be one or more of Zr, Ti, V, Cr, Mn, Ni, Cu, Zn, Nb, Mo, Tc, Cd, Hf, Ta, W, Re, Hg, Tl and the 4f-block lanthanides. Suitable 4f-block lanthanides may optionally be La, Ce, Pr, Nd, Pm, Sm, Eu, Gd, Tb, Dy, Ho, Er, Tm, Yb and/or Lu. The metal for the one or more other metal-based components may optionally for example be one or more of Zn, Cu, Mn, Mo and W. The metal for the one or more other metal-based components may optionally for example be one or more of Re and Pt. The catalyst may optionally comprise from about 0.01 to about 10% in total of other metal(s) (based on the total weight of all the other metals as a percentage of the total weight of the catalyst), or optionally from about 0.1 to about 5% in total of other metals, or optionally about 3% in total of other metals.

The catalyst may optionally comprise a catalyst support. The support may optionally comprise a refractory metal oxide, carbide, nitride, or a mixture of two or more thereof. The support may optionally comprise alumina, zirconia, silica, titania, or a mixture of two or more thereof. Alternatively or additionally, the support may optionally be absent of alumina. The surface of the support may optionally be modified by treating it with silica, titania, zirconia, magnesia, chromia, alumina, or a mixture of two or more thereof. The material used for the support and the material used for modifying the support may optionally be different.

Preferably, the support comprises silica. The surface of the silica may optionally be treated with a refractory solid oxide such as titania. The material used to modify the support may optionally be used to increase the stability (e.g. by decreasing deactivation) of the supported catalyst. The modified support may optionally comprise silica and titania. The material used to modify the support may optionally be used to increase the stability (e.g. by decreasing deactivation) of the supported catalyst.

The catalyst support may optionally comprise up to about 30% by weight of the oxide (e.g., silica, titania, magnesia, chromia, alumina, or a mixture of two or more thereof) used to modify the surface of the support, or from about 1% to about 30% by weight, or from about 2% to about 20% by weight, or from about 3% to about 15% by weight, or from about 4% to about 10% by weight, or from about 5% to about 8% by weight.

The catalyst support may optionally be in the form of a structured shape, pellets, or a powder. The catalyst support may optionally be in the form of particulate solids.

The catalyst may optionally be derived from a catalyst precursor which may optionally be activated to produce the Fischer-Tropsch catalyst, for instance by heating the catalyst precursor in hydrogen and/or a hydrocarbon gas (e.g., methane), or in a hydrogen or hydrocarbon gas diluted with another gas, such as nitrogen and/or methane, to convert at least some of the carbides or oxides to elemental metal. In the active catalyst, the cobalt may optionally be at least partially in the form of its carbide or oxide.

The catalyst may optionally have any size and geometric configuration that fits within the reactor. The catalyst may optionally be in the form of particulate solids (e.g., pellets, powder, fibers, and the like) having a median particle diameter of about 1 to about 1000 μm, or about 10 to about 750 μm, or about 25 to about 500 μm. The median particle diameter may optionally be in the range from 50 to about 500 μm or about 100 to about 500 μm, or about 125 to about 400 μm, or about 170 to about 300 μm. The catalyst may optionally be in the form of a fixed bed of particulate solids.

The catalyst may optionally exhibit a rate of CO hydrogenation greater than about 55 mmol CO per gram of cobalt per hour after at least about 48 hours of operation at about 180° C., with a feed stream of about 10 mol % inert tracer gas, a $H_2/CO$ ratio of about 10 at an absolute pressure of about 354.6 kPa (3.5 atm) and a flow rate such that CO conversion is between about 18% and about 22%.

The catalyst may optionally exhibit a rate of CO hydrogenation greater than about 60 mmol CO per gram of cobalt per hour, or greater than about 65 mmol CO per gram of cobalt per hour, or greater than about 70 mmol CO per gram of cobalt per hour, or greater than about 75 mmol CO per gram of cobalt per hour, or greater than about 80 mmol CO per gram of cobalt per hour, or greater than about 85 mmol CO per gram of cobalt per hour, or greater than about 90 mmol CO per gram of cobalt per hour, after at least about 48 hours of operation at about 180° C., with a feed stream of about 10 mol % inert tracer gas, a $H_2$/CO ratio of about 10 at an absolute pressure of about 354.6 kPa (3.5 atm) and a flow rate such that CO conversion is between about 18% and about 22%.

The catalyst may optionally exhibit a rate of CO hydrogenation greater than about 1.20 mmol CO per mol of cobalt per second, or greater than about 1.25 mmol CO per mol of cobalt per second, or greater than about 1.30 mmol CO per mol of cobalt per second, or greater than about 1.35 mmol CO per mol of cobalt per second, or greater than about 1.40 mmol CO per mol of cobalt per second, or greater than about 1.45 mmol CO per mol of cobalt per second, or greater than about 1.50 mmol CO per mol of cobalt per second, after at least about 48 hours of operation at about 180° C., with a feed stream of about 10 mol % inert tracer gas, a $H_2$/CO ratio of about 10 at an absolute pressure of about 354.6 kPa (3.5 atm) and a flow rate such that CO conversion is between about 18% and about 22%.

According to another aspect of the present invention, there is provided a method of conducting a Fischer-Tropsch reaction in a reactor, comprising:

passing a gas mixture comprising CO and $H_2$ over a catalyst according to the first aspect of the invention.

The reactor may optionally for example be a fixed bed reactor, a continuous stirred tank reactor, a slurry bubble column reactor, a circulating fluidized bed reactor, or a microchannel reactor. Preferably, the reactor is a microchannel reactor. Microchannel reactors are disclosed in WO2016201218, in the name of the present applicant, which is incorporated herein by reference, and similarly in LeViness et al. "Velocys Fischer-Tropsch Synthesis Technology—New Advances on State-of-the-Art", *Top Catal.*, 2014, 57, 518-525.

The inventors have found that the catalysts of the invention are particularly effective in microchannel reactors. It is the ability of microchannel reactors to maintain near isothermal conditions that allows them to capitalize on a higher density of reactive sites in order to achieve product compositions which have a reduced light hydrocarbon selectivity, while maintaining high volumetric productivity.

Furthermore, microchannel reactors are designed to intensify a Fischer-Tropsch reaction compared to conventional reactors e.g., a fixed bed reactor. The catalysts according to the invention, with increased weight % of cobalt and increased packed apparent bulk density, are advantageously more suitable for this intense process than catalysts of the art.

A "microchannel" is a channel having at least one internal dimension (wall-to-wall, not counting catalyst) of 10 mm or less, preferably 2 mm or less, and greater than 1 μm (preferably greater than 10 μm), and in some embodiments 50 to 500 μm; preferably a microchannel remains within these dimensions for a length of at least 10 mm, preferably at least 200 mm. In some embodiments, in the range of 50 to 1000 mm in length, and in some embodiments in the range of 100 to 600 mm. Microchannels are also defined by the presence of at least one inlet that is distinct from at least one outlet. Microchannels are not merely channels through zeolites or mesoporous materials. The length of a microchannel corresponds to the direction of flow through the microchannel. Microchannel height and width are substantially perpendicular to the direction of flow through the channel. In the case of a laminated device where a microchannel has two major surfaces (for example, surfaces formed by stacked and bonded sheets), the height is the distance from major surface to major surface and width is perpendicular to height. Microchannels may optionally be straight or substantially straight—meaning that a straight unobstructed line can be drawn through the microchannel ("unobstructed" means prior to particulate loading). Typically, devices comprise multiple microchannels that share a common header and a common footer. Although some devices have a single header and single footer; a microchannel device can have multiple headers and multiple footers.

Microchannel reactors are characterized by the presence of at least one reaction channel having at least one dimension (wall-to-wall, not counting catalyst) of 10 mm or less, preferably 2 mm or less (in some embodiments about 1 mm or less) and greater than 100 nm (preferably greater than 1 μm), and in some embodiments 50 to 500 μm. A channel containing a catalyst is a reaction channel. More generally, a reaction channel is a channel in which a reaction occurs. Microchannel apparatus is similarly characterized, except that a catalyst-containing reaction channel is not required. Both height and width are substantially perpendicular to the direction of flow of reactants through the reactor. The sides of a microchannel are defined by reaction channel walls. These walls are preferably made of a hard material such as a ceramic, an iron based alloy such as steel, or a Ni-, Co- or Fe-based superalloy such as monel. The choice of material for the walls of the reaction channel may depend on the reaction for which the reactor is intended. The reaction chamber walls may optionally be comprised of a stainless steel or Inconel™ which is durable and has good thermal conductivity. Typically, reaction channel walls are formed of the material that provides the primary structural support for the microchannel apparatus. The microchannel apparatus can be made by known methods, and may optionally be made by laminating interleaved plates (also known as "shims"), and preferably where shims designed for reaction channels are interleaved with shims designed for heat exchange. Some microchannel apparatus include at least 10 layers (or at least 100 layers) laminated in a device, where each of these layers contain at least 10 channels (or at least 100 channels); the device may optionally contain other layers with fewer channels.

Heat exchange fluids may flow through heat transfer channels (preferably microchannels) adjacent to process channels (preferably reaction microchannels), and can be gases or liquids and may optionally include steam, liquid metals, or any other known heat exchange fluids—the system can be optimized to have a phase change in the heat exchanger. Multiple heat exchange layers may optionally be interleaved with multiple reaction microchannels. For example, at least 10 heat exchangers interleaved with at least 10 reaction microchannels and preferably there are 10 layers of heat exchange channel arrays (preferably microchannel arrays) interfaced with at least 10 layers of reaction microchannels. Each of these layers may contain simple, straight channels or channels within a layer may have more complex geometries.

The Fischer-Tropsch reaction is well known and the reaction conditions can be any of those known to the person skilled in the art, for instance the conditions discussed in WO2008104793. For example, the Fischer-Tropsch reaction may optionally be carried out at a temperature of from about 150 to about 300° C., or from about 200 to about 260° C., a pressure of from about 100 to about 10000 kPa, or from about 1500 to about 2500 kPa, a $H_2$ to CO molar ratio of from about 1.1 or about 1.2 to about 2.2, or from about 1.5 to about 2.0, or about 1.8, and a gaseous hourly space velocity of from about 200 to about 5000 hr$^{-1}$, or from about 1000 to about 2000 hr$^{-1}$. In a microchannel reactor, the gaseous hourly space velocity may optionally be from about 5000 to about 30000 hr$^1$.

The contact time of the reactants with the catalyst may optionally range up to about 3600 ms, or up to about 2000 ms, or in the range from about 10 to about 2600 ms, or from about 10 ms to about 2000 ms, or about 20 ms to about 500 ms, or from about 200 to about 450 ms, or from about 240 to about 350 ms.

The space velocity (or gas hourly space velocity (GHSV)) for the flow of the gas mixture in a microchannel reactor may optionally be at least about 1000 hr$^1$ (normal liters of feed/hour/liter of volume within the process microchannels), or at least about 1800 hr$^{-1}$, or from about 1000 to about 1000000 hr$^{-1}$, or from about 5000 to about 20000 hr$^{-1}$.

The pressure within the process microchannels may optionally be up to about 10200 kPa, or in the range from about 100 to about 10200 kPa, or from about 100 to about 7600 kPa, or from about 200 to about 4100 kPa, or from about 200 to about 1100 kPa, or from about 1000 to about 5100 kPa, or from about 2000 to about 3100 kPa.

During a Fischer-Tropsch reaction, the catalyst is gradually degraded by contaminants. Such contaminants can produce either regenerable or non-regenerable deactivation. This catalyst degradation decreases its effectiveness and requires a gradual increase in temperature to offset the activity loss and to maintain acceptable carbon monoxide conversion. This is described in Steynberg et al., "Fischer-Tropsch catalyst deactivation in commercial microchannel reactor operation", *Catalysis Today*, 2018, 299, 10-13.

The operating temperature continues to be increased until the product composition becomes economically unfavorable. At this point, the catalyst activity can be partially recovered through a regeneration which reverses the activity loss caused by regenerable mechanisms. Since non-regenerable deactivation pathways are not reversed, the starting temperature following successive regenerations increases relative to each previous cycle until the temperature operating window for a cycle becomes impractically short and a catalyst exchange is required.

The upper temperature limit is a relatively fixed value. However, by using the catalysts of the invention, the starting temperature can be lowered substantially, allowing for a longer cycle between recovery from regenerable deactivation mechanisms and a longer overall cycle between catalyst exchanges resulting from non-regenerable deactivation mechanisms. By way of a non-limiting example, a 10° C. lower initial operating temperature could extend the overall operating period 300 days or more.

Therefore, the reaction temperature using fresh catalyst may optionally be lower than about 210° C., preferably lower than about 205° C. By "fresh catalyst" it is preferably meant that the catalyst has not previously been used in a Fischer-Tropsch reaction. The reaction temperature using fresh catalyst may also be termed the "starting temperature". Therefore, the starting temperature may optionally be lower than about 210° C., preferably lower than about 205° C.

The conversion of CO from the fresh synthesis gas may optionally be about 70% or higher, or about 75% or higher, or about 80% or higher, or about 90% or higher, or about 91% or higher, or about 92% or higher, or from about 88% to about 95%, or from about 90% to about 94%, or from about 91% to about 93%. If a tail gas recycle is used, the one-pass conversion of CO for the CO in the reactant mixture (i.e., fresh synthesis gas plus recycled tail gas) may optionally be in the range from about 50% to about 90%, or from about 60% to about 85%.

The method may optionally have a C5+ liquid productivity of at least about 0.5 g of liquid per gram of catalyst per hour at a volumetric CO consumption rate of about 50 mmol CO per mL of catalyst per hour. The method may optionally have a C5+ liquid productivity of at least about 1.0 g of liquid per gram of catalyst per hour at a volumetric CO consumption rate of about 100 mmol CO per mL of catalyst per hour.

The products of the reaction, prior to any separation steps, may optionally comprise about 15% or less of methane. The products may optionally comprise about 10% or less, or about 5% or less, of methane. The products may optionally comprise methane in an amount of from about 0.01 to about 10%, or from about 0.1% to about 5%.

The wax product alpha may optionally be greater than about 0.94, preferably greater than about 0.95. The wax product is preferably the C25-C90 wax carbon number products of the Fischer-Tropsch reaction. It is of economic value for alpha to be as large as possible. The inventors have found that the lower reaction temperature, which can be used with the catalysts of the invention, advantageously yields better selectivities, product distributions, and thus a greater value of alpha.

The deactivation rate of the catalyst may optionally be such that it can be used in a Fischer-Tropsch reaction for more than about 300 hours, or more than about 3000 hours, or more than about 12000 hours, or more than about 15000 hours, all before a catalyst rejuvenation or regeneration is required.

The catalyst may optionally have a deactivation rate of less than about 1.6% per day, or less than about 1.4% per day, or less than about 1.2% per day, or less than about 1.0% per day, or less than about 0.8% per day, or less than about 0.6% per day, or less than about 0.4% per day.

According to another aspect of the present invention, there is provided a Fischer-Tropsch reaction system comprising:
  a reactant stream comprising CO and $H_2$; and
  a reactor comprising a catalyst according to the first aspect of the invention.

According to another aspect of the present invention, there is provided a method of making a Fischer-Tropsch catalyst, comprising the steps of:
  a) impregnating greater than 100% of the pore volume of a support with a solution or suspension comprising a cobalt-containing compound; and
  b) drying under heat at a temperature below that of the reflux temperature of the solution or suspension.

Cobalt-containing Fischer-Tropsch catalysts of the art are typically made using incipient wetness impregnation, which does not require step b). However, in order to obtain a catalyst comprising greater than about 40% by weight of cobalt using incipient wetness impregnation, in excess of 8 or 9 impregnation steps are required. This number would be even greater on a commercial scale, which means that a high loading catalyst made using incipient wetness impregnation is unfeasible for scale up, because this would add a manufacturing overhead to catalyst preparation.

FIG. 1 shows the effect of increasing the level of impregnation on the number of synthetic steps required to reach a certain cobalt loading. By way of an example, if a cobalt loading above 50 wt. % is targeted, then 15 synthesis steps will be required when impregnating 90% of the pore volume (which is representative of incipient wetness impregnation).

In order to decrease the number of passes (and limit production costs), the amount of solution per pass has to be increased.

The inventors have surprisingly found that the use of excess wetness impregnation (i.e. greater than 100% of the pore volume of the support), as compared to using incipient wetness impregnation, permits the synthesis of a high loading cobalt catalyst with fewer synthesis steps and lower production costs. It has also been found that the excess wetness impregnation method significantly reduces the number of impregnations required to achieve catalysts in excess of 50% by weight of cobalt. Furthermore, these catalysts surprisingly retain an extremely high efficiency, despite the high cobalt loading and the wet initial impregnation condition.

Step a) may optionally comprise impregnating greater than 105%, or greater than 110%, or greater than 115%, or greater than 120%, or greater than 125%, or greater than 130%, or greater than 135%, of the pore volume of a support with a solution or suspension comprising a cobalt-containing compound.

Suitable cobalt-containing compounds include cobalt benzoylacetonate, cobalt carbonate, cobalt cyanide, cobalt hydroxide, cobalt oxalate, cobalt oxide, cobalt nitrate, cobalt acetate, cobalt acetylacetonate and cobalt citrate. These cobalt compounds can be used individually or in combination. These cobalt compounds may optionally be in the form of hydrates or in anhydrous form. In some cases, where the cobalt compound is not soluble in water, such as cobalt carbonate or cobalt hydroxide, a small amount of nitric acid or a carboxylic acid may optionally be added to enable the compound to fully dissolve in an aqueous solution or suspension. Preferably, the cobalt-containing compound is cobalt nitrate hexahydrate.

Preferably, the cobalt-containing compound, for example cobalt nitrate, reacts with a complexing agent, such as citric acid, during calcination. The citric acid may optionally act as a complexing agent and/or as a fuel (i.e. reducing agent for cobalt nitrate) in the calcination reaction.

Suitable complexing agents for use in the method are the polar organic compounds. Preferred complexing agents are urea, carboxylic acids such as acetic acid, citric acid, glycolic acid, malic acid, propionic acid, succinic acid, lactic acid, and oxalic acid. Mixtures of complexing agents may optionally also be used. Preferably, the complexing agent is citric acid.

Step b) is performed at a temperature below that of the reflux temperature of the solution or suspension. It is essential that reflux does not occur, otherwise this would cause condensed water to wash into the drying material and reduce the homogeneity of the impregnated cobalt salt. The temperature may optionally be in the range of from about 80° C. to about 100° C., or from about 90° C. to about 95° C. The duration of step b), when at the desired temperature, may optionally be from about 1 min to about 60 mins, or from about 5 mins to about 50 mins, or from about 10 mins to about 40 mins, or from about 15 mins to 30 mins.

The inventors have also found that it is important for the drying to be homogeneous, and to ensure that there are no thermal gradients where dried catalyst will pull impregnating solution from undried catalyst.

Step b) may optionally be performed until the catalyst is free-flowing. It is beneficial for the catalyst to be free-flowing prior to calcination for easy transfer.

The support onto which the solution or suspension has been impregnated may optionally be calcined, preferably at a temperature in the range from about 200° C. to about 350° C., more preferably from about 200° C. to about 250° C. In other words, the method may optionally further comprise step c) calcinating the impregnated support. Calcining may optionally take place in a box oven, furnace or rotary calciner. In one non-limiting example, calcining takes place by heating at a temperature that increases at a ramp rate of 2° C./min up to a final temperature of 250° C. The temperature is held at 250° C. for about 3 hours. In another non-limiting example, calcining takes place by heating at a temperature that increases at a ramp rate of 2° C./min up to a temperature of 200° C.; the temperature is held at 200° C. for about 3 hours before being increased again at a ramp rate of 1° C./min up to a temperature of 250° C. and then held at that temperature for a further 3 hours. The final temperature preferably does not exceed about 400° C., because calcining at higher temperatures may have the effect of reducing catalyst stability.

Steps a), b) and c), if present, may optionally be repeated one or more times. Steps a), b) and c), if present, may optionally be repeated 1, 2, 3, 4, 5, 6, 7, 8, 9 or 10 times. For each repetition, the solution or suspension used in the deposition step may optionally be the same or different. If the solution or suspension in each repetition is the same, the repetition of the steps allows the amount of catalyst metal(s) to be brought up to the desired level on the support stepwise in each repetition. If the solution or suspension in each repetition is different, the repetition of the steps allows schemes for bringing the amounts of different catalyst metals up to the desired level in a series of steps to be executed.

According to another aspect of the present invention, there is provided a method of making a Fischer-Tropsch catalyst according to the first aspect of the invention, comprising the steps of:
  a) impregnating greater than 100% of the pore volume of a support with a solution or suspension comprising a cobalt-containing compound; and
  b) drying under heat at a temperature below that of the reflux temperature.

According to another aspect of the present invention, there is provided a Fischer-Tropsch catalyst made by a method comprising the steps of:
  a) impregnating greater than 100% of the pore volume of a support with a solution or suspension comprising a cobalt-containing compound; and
  b) drying under heat at a temperature below that of the reflux temperature.

For the avoidance of doubt, all features relating to the catalyst may optionally apply, where appropriate, to the method of conducting a Fischer-Tropsch reaction, to the reaction system, and to the method of making a Fischer-Tropsch catalyst, and vice versa.

BRIEF DESCRIPTION OF THE DRAWINGS

Preferred embodiments of the invention are described below by way of example only with reference to FIGS. 1 to 3 of the accompanying drawings, wherein.

DETAILED DESCRIPTION

Catalyst Synthesis

Figure 1:
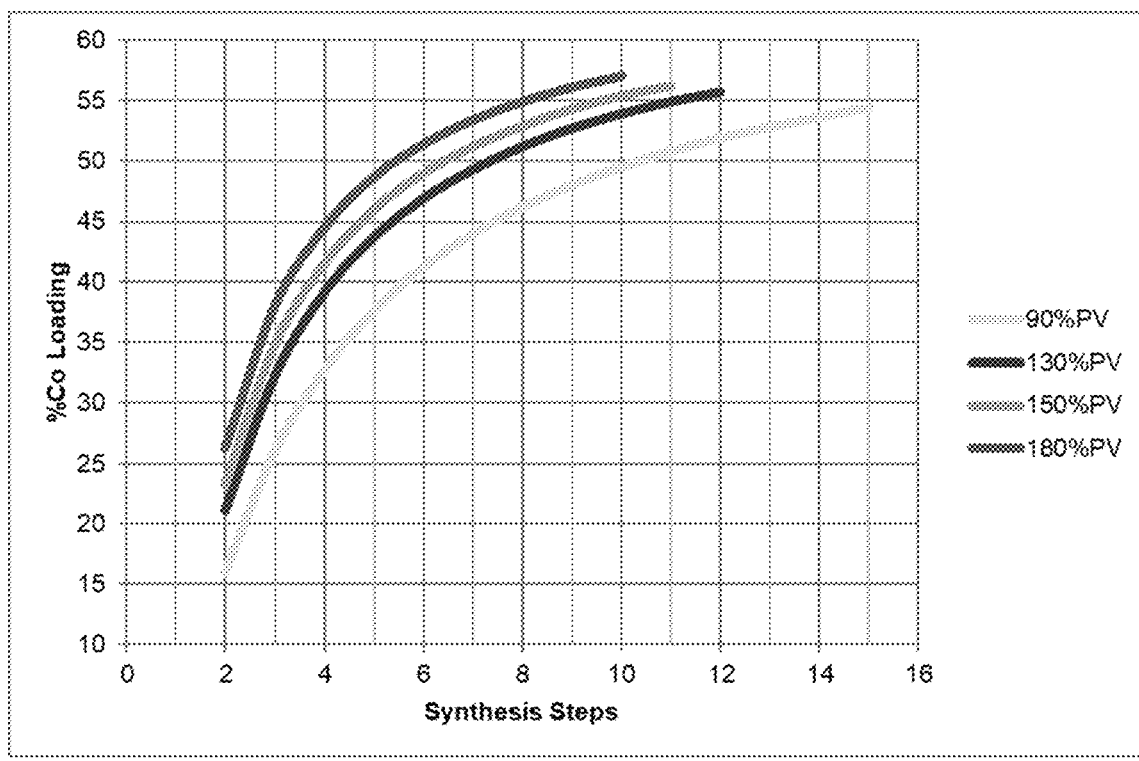
FIG. 1 illustrates the effect of increasing the level of impregnation on the number of synthetic steps required to reach a certain cobalt loading.

The synthesis of comparative catalyst 1 in Table 3 is outlined below. Catalysts 1 to 11 in Tables 3 and 4, which fall within the scope of the invention, were made in a similar way, but with varying amounts of Co, Ti and Re, and on both PD12058 and LC150 (which are different batches of silica).

Materials

Table 2 outlines the materials used in the synthesis of the catalysts.

TABLE 2

| Materials | Purity/Concentration | Supplier |
|---|---|---|
| Silica (LC150/PD12058) | — | Grace/PQ |
| Titanium(IV) bis(ammonium lactato)dihydroxide (TALH) | 50% | Sigma |
| Citric acid monohydrate | 99 wt. % | Sigma |
| Cobalt nitrate hexahydrate | 98 wt. % | Sigma |
| $HReO_4$ sol. | 75 wt. % | Sigma |
| $Pt(NH_3)_4(OH)_2$ sol. | 9.96 wt. % | Alfa Aesar |

Preparation of Modified Support 16 g of PD12058 was weighed out and placed in a fan oven at 100° C. for 2 hours to dry. 11.66 g of the hot silica was immediately weighed into an alumina bowl, covered and allowed to cool to room temperature. 2.5 g of citric acid was weighed out and mixed with 1.2 mL of deionized water under heat to 50° C. until fully dissolved. 11.54 g of TALH was then weighed and added to the cooled citric acid solution and mixed until homogeneous. The mixture was poured into a graduated cylinder, the beakers rinsed out with 1 mL of deionized water and the volume adjusted to 25.2 mL. The solution was added to cooled silica in 4 aliquots with stirring after each addition until the mixture was homogeneous and the liquid absorbed. After the final addition, the impregnated silica was transferred to a weighed crucible and spread evenly over the crucible surface, so that material did not exceed 10 mm depth. The crucible was transferred to a muffle furnace and dried/calcined using the following program: 2° C./min to 100° C. and hold for 5 hours, then 2° C./min to 250° C. and hold for 5 hours. Once material was calcined and cooled to below 50° C. the weight of the sample was taken and compared to the expected material weight to calculate the purity of the support.

Catalyst Synthesis 9.1 g of the modified support material from the previous step was weighed out into an alumina bowl. 12.47 g of cobalt nitrate hexahydrate was weighed, 3.1 mL of deionized water added, and the mixture heated to 50° C. on a hotplate with stirring until fully dissolved. 0.2698 g of perrhenic acid was weighed out and added to the cobalt nitrate solution with stirring. The solution was poured into a graduated measuring cylinder and the volume adjusted to 11.5 mL with deionized water. Once cool to room temperature the solution was added to the modified support in 4 aliquots with stirring after each addition until the mixture was homogeneous and the liquid absorbed.

After the final addition, the impregnated support was transferred to a weighed crucible and spread evenly over the crucible surface so that material did not exceed 10 mm depth. The crucible was then transferred to a muffle furnace and dried/calcined using the following program: 2° C./min to 100° C. and hold for 5 hours, then 2° C./min to 200° C. and hold for 3 hours, followed by 1° C./min to 250° C. and hold for 3 hours. Once calcined and cooled, the cobalt impregnation described above was repeated with the addition of 1.79 g of citric acid to the cobalt nitrate solution prior to impregnation. The calcination program of this additional step was: 2° C./min to 100° C. and hold for 5 hours then 2° C./min to 250° C. and hold for 3 hours.

The final step of the synthesis was the addition of platinum as a promotor. 0.4518 g of tetraamine platinum hydroxide was weighed out and rinsed into a graduated cylinder, and the solution topped up with water to 10.7 mL. The solution was then added to the dried and calcined material from the last step in 4 aliquots with stirring after each addition until mixture was homogeneous and the liquid absorbed.

After the final addition, the impregnated support was transferred to a weighed crucible and spread evenly over the crucible surface so that material did not exceed 10 mm depth. The crucible was then transferred to a muffle furnace and dried/calcined using the following program: 2° C./min to 100° C. and hold for 5 hours, then 2° C./min to 250° C. and hold for 3 hours. Once cool the finished catalyst was weighed and transferred to a labelled bottle.

Excess Wetness Impregnation

For the drying of excess wetness impregnated catalysts, a rotary evaporator was adapted into a rotary drying unit. This allowed the impregnated catalyst to be dried under heating and mixed in a rotary paddle flask broadly simulating the action of an industrial paddle drying. To prevent reflux, a vacuum tube was held at the base of the neck inside the vessel creating airflow into the open vessel and out the vacuum tube, along with any evaporating moisture. Mineral oil was used as the heating medium in the heating bath to allow for a greater range of temperatures than would be allowed by water.

By way of an example, a catalyst according to the invention (42.0% Co, 0.2% Re, 0.03% Pt on 10% $TiO_2$/AGC) was prepared by impregnating the support with excess liquid impregnation followed by drying in the simulated-paddle drying apparatus to reduce the solution volume to such a point that the impregnated material was free flowing within the paddle flask. Tests were conducted on 75 mL of support to give enough material to allow for appropriate mixing by the paddles. For the drying, the oil bath was preheated to 60° C. For each step, the catalyst support was impregnated in the drying flask to minimize losses during transfer. The flask was then attached to the setup, rotated at 20 rpm, airflow started, and the oil bath was heated to 90-95° C. at approximately 1° C./min and held until the impregnated catalyst became free flowing, typically taking 15-30 minutes while at temperature. The dried impregnated catalyst was then calcined in a muffle furnace using the heating procedure described above.

Measuring Packed Apparent Bulk Density

Packed apparent bulk density (PABD) is measured in a graduated cylinder of 5 mL volume. However, a graduated cylinder of any reasonable volume (for example 5 mL, 25 mL, 100 mL, or 250 mL) can be used without any significant difference in result (i.e., no more than 1% difference). The cylinder is filled with catalyst and hand tapped to settle the solid and more material added, tapped, etc. until the amount just approaches 5 mL. The graduate is then fitted onto a Quantachrome Autotap DAT-4 instrument and subjected to 1500 taps. The settled volume of the catalyst is determined and then the catalyst mass is determined. The packed apparent bulk density is calculated by dividing the weight of catalyst in grams by the volume in mL after 1500 taps. The packed apparent bulk density of cobalt is calculated by multiplying the packed apparent bulk density of the catalyst by the weight % of cobalt in the catalyst.

The above method is generally in accordance with the procedures of ASTM D7481-09 (i.e., D7481 approved or reapproved in 2009): Standard Methods for determining loose and tapped bulk densities of powders using a graduated cylinder.

Preferably, the measured catalyst mass is a dry mass. Since the tapping process takes time, the catalyst will collect moisture from the atmosphere to varying extents, depending on relative humidity, prior exposure, and time of exposure. If an "undried" mass is measured, the packed apparent bulk density of cobalt will be overestimated. This is because accumulated moisture increases the mass of a given volume of catalyst by the amount of water collected, resulting in an inflation of the packed apparent bulk density of cobalt by the relative moisture content. Therefore, to ensure accurate and consistent results, it is preferable for measurements to be made on a "dry" basis. The dry mass may optionally be measured using a moisture balance, which includes a heating stage for removing adsorbed moisture.

Within a microchannel reactor, the packed apparent bulk density of cobalt may optionally be determined by densifying the charge within the microchannels of the reactor using a suitable method (such as those disclosed in WO2013013077, in the name of the present applicant, which is incorporated herein by reference), determining the total mass of catalyst charged, and from this deriving the charged reactor packed apparent bulk density of cobalt.

Catalysts and Fixed Bed Reactor Test Results

Table 3 illustrates nine catalysts that were synthesized according to the invention, as well as a comparative catalyst known in the art. The weight percent of cobalt in the catalysts of the invention varied from 43% to 53%, with a packed apparent bulk density of at least 1.32 g/mL.

For the fixed bed reactor test, a catalyst sample of volume of 0.1285 mL was diluted with 2.184 mL of SiC (1:18 volume ratio) and loaded into a reactor. The catalyst was activated by flowing $H_2$ at 400° C. for two hours, at atmospheric pressure and a GHSV of 15000 $hr^{-1}$. After activation, the reactor was cooled to 165° C. and the gas flow switched to synthesis gas ($H_2$:CO 2:1, 5% $N_2$ diluent) before holding at this temperature for 2 hours. The pressure was then increased to 2000 kPa (20 bar), and the reactor temperature was then ramped to the target test temperature of 205° C. The test was run for 140 hours. Deactivation was measured in the periods of from 0 hours to 24 hours and from 116 hours to 140 hours, with the conversions and selectivities noted at 24 and 140 hours.

As can be seen from the fixed bed reactor test results in Table 3, all of the catalysts according to the invention exhibited a significantly higher CO conversion than the comparative example. The highest CO conversation was observed with catalyst #9, which contains 53% by weight of cobalt, and has a packed apparent bulk density of 1.63 g/mL and a packed apparent bulk density of cobalt of 0.86 g/mL. Furthermore, all of the catalysts according to the invention exhibited a lower deactivation rate than the comparative example and, as such, can be used for a longer period of time in a Fischer-Tropsch reaction before regeneration is required.

Table 4 illustrates two catalysts that were synthesized according to the invention, as well as a several comparative catalysts. C2-C14 represent ActOCat 1200, which is a catalyst known in the art. The reference catalyst (#C2) has a PABD of cobalt of 0.426 g/ml, comparative catalysts #C3-C14 have a PABD of cobalt of 0.596 g/ml and the catalysts according to the invention (#10-11) have a PABD of cobalt of 0.784 g/ml.

The final column in Table 4 is the cobalt time yield (CTY), which is the moles of CO converted per mole of cobalt in the sample per unit time, and is representative of the efficiency of the catalyst.

Comparing C2 with C3-C14 in Table 4, as expected it can be seen that increasing the catalyst PABD, and thus increasing the PABD of cobalt, increases the moles of CO converted per mL of catalyst, per hour (from 29 mmol CO $ml^{-1}$ $h^{-1}$ to 37-44 mmol CO $ml^{-1}$ $h^{-1}$). However, the efficiency of the catalyst (the CTY) does not increase and remains approximately the same (1.1 mmol CO mol $Co^{-1}$ $s^{-1}$ compared to 1.00-1.2 mmol CO mol $Co^{-1}$ $s^{-1}$).

However, comparing #10-11 with C2-C14 in Table 4, it can be seen that increasing the catalyst PABD, and thus increasing the PABD of cobalt, increases both the moles of CO converted per mL of catalyst per hour, and the efficiency of the catalyst. The efficiency (CTY) increases from to 1.00-1.2 mmol CO mol $Co^{-1}$ $s^{-1}$ in the comparative catalysts to approximately 1.5 mmol CO mol $Co^{-1}$ $s^{-1}$ in the catalysts according to the invention. Therefore, the catalysts of the invention not only increase the PABD of cobalt in the catalyst, such that the moles of CO converted increases, but do so in a way that is considerably more efficient than catalysts of the art.

This is achieved through use of the method of making a Fischer-Tropsch catalyst according to the invention. Catalysts #12-13 were made using AGC silica and the excess liquid impregnation method, wherein the support is impregnated 130% of the pore volume of the support. Therefore, the method of making a Fischer-Tropsch catalyst according to the invention results in catalysts which are more efficient than catalysts of the art.

TABLE 3

| | | | Catalyst composition | | | | | Fixed bed reactor test results | | | | | | | |
|---|---|---|---|---|---|---|---|---|---|---|---|---|---|---|---|
| # | Catalyst ID | Silica | Co wt. % | Ti wt. % | Re wt. % | Pt wt. % | No. steps | PABD (g/mL) | ρ Co (g/mL) | XCO (t1) | XCO (t2) | Deactivation Rate (%/day) | C5+ (t1) | C5+ (t2) | CH4 (t1) | CH4 (t2) |
| C1 | 1401-28-009-1 | PD12058 | 33 | 6.5 | 0.2 | 0.03 | 4 | 0.67 | 0.22 | 34.48 | 29.76 | −0.86 | 87.1 | 84.92 | 7.29 | 8.03 |
| 1 | 1402-17-013-1 | LC150 2 | 48 | 5.5 | 0.3 | 0.015 | 8 | 1.32 | 0.63 | 71.8 | 69.3 | −0.56 | 87.3 | 85.3 | 9.1 | 9.1 |
| 2 | 1402-21-051-1 | LC150 2 | 48 | 5.5 | 0.1 | 0.045 | 8 | 1.33 | 0.63 | 69.94 | 70.57 | 0.04 | 85.1 | 85.02 | 9.25 | 9.01 |
| 3 | 1402-21-051-2 | PD12058 | 43 | 6.5 | 0.2 | 0.03 | 8 | 1.49 | 0.64 | 67.03 | 70.27 | 0.56 | 84.93 | 83.89 | 10.32 | 9.94 |
| 4 | 1403-27-009-1 | LC150 1 | 48 | 5.5 | 0.1 | 0.015 | 8 | 1.37 | 0.65 | 76.7 | 74.9 | −0.45 | 87.1 | 85 | 9.6 | 9.4 |
| 5 | 1402-07-009-2 | LC150 1 | 48 | 5.5 | 0.3 | 0.045 | 8 | 1.42 | 0.68 | 77.27 | 75.27 | −0.38 | 85.86 | 84.32 | 10.45 | 10.1 |
| 6 | 1402-17-013-2 | LC150 1 | 48 | 7.5 | 0.3 | 0.015 | 8 | 1.44 | 0.69 | 68.4 | 67.9 | −0.25 | 84.3 | 83 | 11.6 | 11 |
| 7 | 1403-26-009-3 | LC150 1 | 48 | 7.5 | 0.1 | 0.045 | 8 | 1.45 | 0.69 | 71.6 | 71.8 | −0.16 | 84.9 | 83.1 | 11 | 10.7 |

TABLE 3-continued

| | | | Catalyst composition | | | | | Fixed bed reactor test results | | | | | | | |
|---|---|---|---|---|---|---|---|---|---|---|---|---|---|---|---|
| # | Catalyst ID | Silica | Co wt. % | Ti wt. % | Re wt. % | Pt wt. % | No. steps | PABD (g/mL) | ρ Co (g/mL) | XCO (t1) | XCO (t2) | Deactivation Rate (%/day) | C5+ (t1) | C5+ (t2) | CH4 (t1) | CH4 (t2) |
| 8 | 1403-26-009-2 | LC150 2 | 48 | 7.5 | 0.1 | 0.015 | 8 | 1.45 | 0.69 | 68.4 | 70.4 | 0.1 | 86.1 | 84.3 | 9.9 | 9.8 |
| 9 | 1402-07-009-1 | PD12058 | 53 | 6.5 | 0.2 | 0.03 | 8 | 1.63 | 0.86 | 80.76 | 79.03 | −0.35 | 86.77 | 84.59 | 9.84 | 10.1 |

PABD = Packed apparent bulk density

TABLE 4

| | Catalysts | | | | Methanation Results | | |
|---|---|---|---|---|---|---|---|
| # | Catalyst | Cat. ID | PABD (g ml$^{-1}$) | g Co ml$^{-1}$ | mmol CO ml$^{-1}$ h$^{-1}$ | mmol CO gCo$^{-1}$ h$^{-1}$ | mmol CO mol Co$^{-1}$ s$^{-1}$ |
| C2 | Reference | 1412-03-003-2 | 0.99 | 0.426 | 29.153 | 68.434 | 1.101 |
| C3 | ActOCat 1200 + 3 w/o Pt | 1609-27-059-4 | 1.25 | 0.596 | 37.268 | 62.530 | 1.006 |
| C4 | ActOCat 1200 + 3 w/o Pt | 1609-27-059-4 | 1.25 | 0.596 | 37.306 | 62.594 | 1.007 |
| C5 | ActOCat 1200 + 3 w/o Pt | 1609-27-059-4 | 1.25 | 0.596 | 37.412 | 62.773 | 1.010 |
| C6 | ActOCat 1200 + 3 w/o Pt | 1609-27-059-4 | 1.25 | 0.596 | 37.549 | 63.003 | 1.013 |
| C7 | ActOCat 1200 + 3 w/o Pt | 1609-27-059-4 | 1.25 | 0.596 | 40.100 | 67.282 | 1.082 |
| C8 | ActOCat 1200 + 3 w/o Pt | 1609-27-059-4 | 1.25 | 0.596 | 41.552 | 69.718 | 1.121 |
| C9 | ActOCat 1200 + 3 with Pt | 1611-28-059-4 | 1.25 | 0.596 | 41.397 | 69.459 | 1.117 |
| C10 | ActOCat 1200 + 3 with Pt | 1611-28-059-4 | 1.25 | 0.596 | 41.937 | 70.364 | 1.132 |
| C11 | ActOCat 1200 + 3 with Pt | 1611-28-059-4 | 1.25 | 0.596 | 42.576 | 71.435 | 1.149 |
| C12 | ActOCat 1200 + 3 with Pt | 1611-28-059-4 | 1.25 | 0.596 | 42.959 | 72.079 | 1.159 |
| C13 | ActOCat 1200 + 3 with Pt | 1611-28-059-4 | 1.25 | 0.596 | 44.530 | 74.715 | 1.202 |
| C14 | ActOCat 1200 + 3 with Pt | 1611-28-059-4 | 1.25 | 0.596 | 44.589 | 74.815 | 1.203 |
| 10 | Present Invention | 1504-30-055-1 | 1.48 | 0.784 | 72.516 | 92.447 | 1.487 |
| 11 | Present Invention | 1504-30-055-1 | 1.48 | 0.784 | 73.284 | 93.427 | 1.503 |

Poisoning Resistance

Poisoning by reactive nitrogen compounds is unusual in that they are not "fatal", but rather produce a deactivation of the catalyst which eventually saturates at a non-zero catalyst activity. The exact saturation activity is dependent on both the catalyst and reactor type being used, but is typically in the region of 30% to 50% of the fresh catalyst activity.

Figure 2:
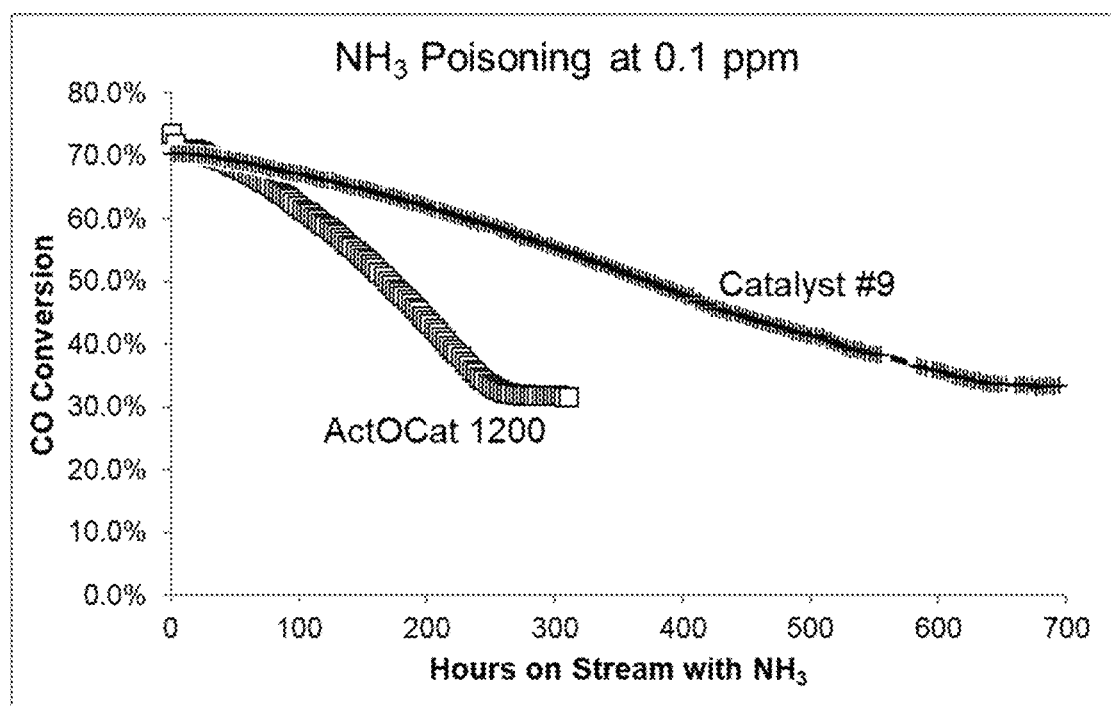
FIG. 2 illustrates the time required for two catalysts to lose activity when exposed to the same burden of the regenerable poison $NH_3$.

FIG. 2 compares the poisoning resistance of catalyst #9 with comparative example ActOCat 1200, which is a catalyst known in the art having 43% by weight of cobalt. Catalyst #9, with 53% by weight of cobalt, has roughly 184% the PABD of cobalt in the reactor compared to the comparative example.

As can be seen in the figure, the ActOCat 1200 catalyst experiences saturated deactivation after about 250 hours of exposure. In contrast, catalyst #9 does not reach saturated deactivation until about 640 hours of exposure, or about 2.5 times as long, with the same $NH_3$ feed level. This illustrates the vastly improved poisoning resistance of the catalysts of the invention compared to those in the art.

Figure 3:
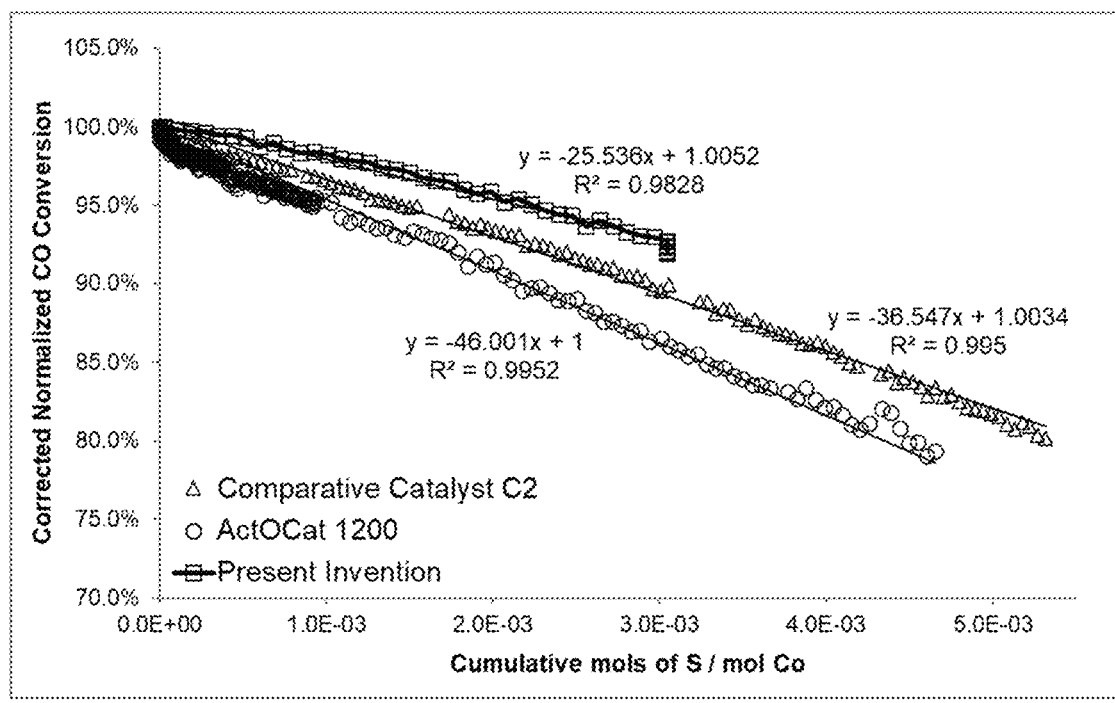
FIG. 3 illustrates CO conversion versus flux of $H_2S$ for three different catalysts.

FIG. 3 demonstrates the improved resistance to sulfur poisoning of the catalysts of the invention. The average amount of sulfur exposed to the catalyst is approximately $2.9 \times 10^{-3}$ molsS/molCo (which is about the same exposure expected at a dosing of 5 ppbv for a 2 yr life).

As can be seen in the figure, at the same flux of $H_2S$, the rate at which CO conversion declines is significantly less for the high cobalt-containing catalyst of the invention compared to the comparative ActOCat 1200 catalyst. The catalysts of the invention can accommodate $H_2S$ better than the comparative catalyst because of the higher cobalt surface area per packed volume of catalyst in the reactor.

Operating Temperature

Catalyst #9 in Table 3 was used in a Fischer-Tropsch reaction and compared to ActOCat 1200. Catalyst #9 contains 53% by weight of cobalt, whereas ActOCat 1200 contains 43% by weight of cobalt, and thus has a lower PABD of cobalt.

The reaction conditions were as follows: Feed $H_2$:CO=1.77, 32% inerts, 290 ms contact time, 2.461 MPa (357 psig) inlet pressure. C15 and C16 both used ActOCat 1200, but with a slightly different average reactor temperature.

TABLE 5

| | | ActOCat 1200 | |
|---|---|---|---|
| Catalyst # | 9 | C15 | C16 |
| Hours on stream | 214 | 215 | 217 |
| Avg. reactor T (° C.) | 202.5 | 212 | 210 |
| CO conversion | 74.0% | 73.0% | 73.9% |
| CH4 selectivity | 6.4% | 6.6% | 6.4% |
| CO2 selectivity | 0.0% | 0.4% | 0.4% |
| C2 selectivity | 0.6% | 0.8% | 0.6% |
| C3 selectivity | 1.8% | 2.1% | 1.8% |
| C4 selectivity | 2.0% | 2.4% | 2.3% |
| C5+ selectivity | 89.2% | 87.8% | 88.5% |
| Wax alpha | 0.943 | 0.933 | — |

As can be seen from Table 5, the comparative data indicates that catalyst #9 uses a reactor temperature that is lower by approximately 8-10° C. for an identical performance (i.e. identical activity) under the same operating conditions.

Furthermore, the lower operating temperature used with catalyst #9 provides an alpha number improvement of approximately 0.07-0.10, as analyzed for the C25-C90 wax carbon number range. As discussed earlier, this advantageously increases the economic value of the products of the reaction.

A further consequence of the lower operating temperature used by catalyst #9, compared to catalysts of the art, is a longer time before regeneration is required, thus increasing the economic value of the reaction process.

The invention claimed is:

1. A Fischer-Tropsch catalyst comprising greater than about 40% by weight of cobalt, and having a packed apparent bulk density greater than about 1.30 g/mL.

2. The catalyst according to claim 1 wherein the catalyst has a packed apparent bulk density of cobalt greater than about 0.60 g/mL, or greater than about 0.65 g/mL, or greater than about 0.70 g/mL, greater than about 0.75 g/mL, or greater than about 0.80 g/mL.

3. The catalyst according to claim 1 wherein the catalyst comprises greater than about 45% by weight, or greater than about 50% by weight, of cobalt.

4. The catalyst according to claim 1 wherein the catalyst has a packed apparent bulk density greater than about 1.35 g/mL, or greater than about 1.40 g/mL, or greater than about 1.45 g/mL, or greater than about 1.50 g/mL, or greater than about 1.55 g/mL, or greater than about 1.60 g/mL.

5. The catalyst according to claim 1 wherein the catalyst has an average cobalt particle size of from about 5 nm to about 20 nm.

6. The catalyst according to claim 1 wherein the catalyst comprises less than about 3% by weight, or less than about 1% by weight, or less than about 0.5% by weight, of noble metals.

7. The catalyst according to claim 6 wherein the noble metals comprise rhenium and/or platinum.

8. The catalyst according to claim 1 wherein the catalyst comprises a catalyst support.

9. The catalyst according to claim 8 wherein the catalyst support comprises silica.

10. The catalyst according to claim 8 wherein the catalyst support comprises an oxide, optionally titania oxide.

11. The catalyst according to claim 10 wherein the catalyst support comprises up to about 30% by weight of the oxide.

12. The catalyst according to claim 8 wherein the catalyst support is absent of alumina.

13. The catalyst according to claim 1 wherein the catalyst exhibits a rate of CO hydrogenation greater than about 55 mmol, or about 60 mmol, or about 65 mmol, or about 70 mmol, or about 75 mmol, or about 80 mmol, or about 85 mmol, or about 90 mmol, CO per gram of cobalt per hour after at least about 48 hours of operation at about 180° C., with a feed stream of about 10 mol % inert tracer gas, a $H_2$/CO ratio of about 10 at an absolute pressure of about 354.6 kPa (3.5 atm) and a flow rate such that CO conversion is between about 18.0% and about 22%.

* * * * *